United States Patent
Berrigan

(12) 
(10) Patent No.: US 6,319,245 B1
(45) Date of Patent: Nov. 20, 2001

(54) DRUG DELIVERY MEANS

(76) Inventor: Thomas John Berrigan, 38 Dumfries Road, Floreat, Western Australia (AU), 6014

( * ) Notice: Subject to any disclaimer, the term of this patent is extended or adjusted under 35 U.S.C. 154(b) by 0 days.

(21) Appl. No.: 09/269,950

(22) PCT Filed: Sep. 24, 1997

(86) PCT No.: PCT/AU97/00633
§ 371 Date: Apr. 8, 1999
§ 102(e) Date: Apr. 8, 1999

(87) PCT Pub. No.: WO98/15306
PCT Pub. Date: Apr. 16, 1998

(30) Foreign Application Priority Data
Oct. 9, 1996 (AU) .................................. PO 2956

(51) Int. Cl.[7] .................................... A61K 9/22
(52) U.S. Cl. ................ 604/891.1; 604/131; 604/181
(58) Field of Search ................... 604/9–10, 93, 604/95, 131–132, 151, 153, 175, 185, 118, 122–124, 890.1, 891.1

(56) References Cited

U.S. PATENT DOCUMENTS

| | | |
|---|---|---|
| 4,525,165 | 6/1985 | Fischell . |
| 4,588,394 | 5/1986 | Schulte et al. . |
| 4,681,560 | 7/1987 | Schulte et al. . |
| 4,714,462 | 12/1987 | DiDomenico . |
| 4,813,951 | 3/1989 | Cannon . |
| 5,053,031 * | 10/1991 | Borsanyi ............................ 604/891.1 |
| 5,085,644 | 2/1992 | Watson et al. . |
| 5,137,529 | 8/1992 | Watson et al. . |
| 5,607,418 * | 3/1997 | Arzbaecher ........................ 604/891.1 |
| 5,871,478 * | 2/1999 | Berrigan ............................ 604/891.1 |

FOREIGN PATENT DOCUMENTS

| | | |
|---|---|---|
| 202696 | 11/1986 | (EP) . |
| 0 335671 A1 | 10/1989 | (EP) . |
| 335671 | 10/1989 | (EP) . |
| 342946 | 11/1989 | (EP) . |
| 342946 A2 | 11/1989 | (EP) . |
| 420620 | 4/1991 | (EP) . |
| 488701 | 6/1992 | (EP) . |
| WO 87/06473 | 11/1987 | (WO) . |
| WO 95/04571 | 2/1995 | (WO) . |

* cited by examiner

Primary Examiner—Sharon Kennedy
Assistant Examiner—Catherine Serke
(74) Attorney, Agent, or Firm—Ladas & Parry

(57) ABSTRACT

A drug delivery means comprising a holding reservoir (11), a pumping means (16), a delivery reservoir (23) and outlet (25), said holding reservoir (11) being connected to the delivery reservoir (23) through the pump (16) where the pump (16) is operable manually to effect transfer of fluid from the holding reservoir (11) to the delivery reservoir (23), the delivery reservoir (23) being connected to the outlet (25) through a flow restriction means (27) which controls the flow to the outlet (25), the delivery reservoir being formed to be resiliently expandable to a maximum volume and wherein the connection between the holding reservoir (11) and delivery reservoir (23) prevents pressurisation of the delivery reservoir (23) substantially beyond a predetermined pressure which will be achieved on the delivery reservoir (23) obtaining its maximum volume, a control means (30) provided with the delivery reservoir to prevent further pressurisation of the delivery reservoir (23) substantially beyond the predetermined pressure, said delivery reservoir (23) being accommodated within the holding reservoir (11).

19 Claims, 6 Drawing Sheets

Graphic Representation

High Capacity Pressure Reservoir
Low Flow Relative to Capacity

Graphic Representation

High Capacity High Pressure Reservoir
Flow High Relative to Reservoir

Graphic Representation    Four Hourly Activation

DRUG DELIVERY MEANS

The present invention relates to a drug delivery means.

In the treatment of patients it is often desirable to provide a means whereby a drug or a like agent can be introduced in a controlled manner over an extensive period of time. This is particularly the case in the treatment of patients suffering from constant pain as in the case of terminally ill patients who require a controlled delivery of an analgesic to be administered in order for them to be able to withstand the pain. In many cases it is desirable that the patient be able to administer the analgesic according to the patients needs.

In other instances it is necessary that the patient receive a drug or like agent at regular or irregular periods which in the past has required self injection by the patient or the patient's carers In the past several devices have been proposed for controlling the introduction of a drug into the body whereby it can be delivered in a controlled manner over a period of time. Such devices have comprised pumps driven by a power source which controls the delivery of drug to the body. Some of these pumps may be mounted externally to the body and are connected to a catheter introduced to the body of the patient. Other devices have comprised a pump which is mounted subcutaneously to the body of the patient and which delivers the drug to the body at a desired location. Such devices suffer the disadvantage however that they are quite expensive and that they utilise a power source in order to effect delivery of the drug. In the event of the failure of the power source the pump must be replaced. The power source has in the past taken a variety of forms including utilisation of a phase change fluid as in the case of a device marketed under the trade mark "INFUSAID".

The present invention comprises a development of the drug delivery means which is the subject of patent application PCT/AU94/00469 and may be mounted either externally or subcutaneously within the body of the patient and which can be controlled by the patient for the administration of a drug or like agent for the long term reduction of pain and/or the treatment of an ailment whereby the drug or agent can delivered continuously or periodically as required.

According the invention resides in a drug delivery means comprising a holding reservoir, a pumping means, a delivery reservoir and an outlet, said holding reservoir being connected to the delivery reservoir through the pump where the pump is operable manually to effect transfer of fluid from the holding reservoir to the delivery reservoir, the delivery reservoir being connected to the outlet through a flow restriction means which controls the flow to the outlet, the delivery reservoir being formed to be resiliently expandable to a maximum volume and wherein the connection between the holding reservoir and the delivery reservoir prevents pressurisation of the delivery reservoir substantially beyond a predetermined pressure which will be achieved on the delivery reservoir obtaining its maximum volume, a control means provided with the delivery reservoir to prevent further pressurisation of the delivery reservoir substantially beyond the predetermined pressure, said delivery reservoir being accommodated within the holding reservoir.

The invention may be positioned externally of the body of the patient or subcutaneously.

Other prior art delivery devices have comprised a manually operated pump which may be mounted externally to the body or subcutaneously in the body of the patient whereby the pump can be activated by the patient for the delivery of the drug as the need arises. Examples of such devices are disclosed in U.S. Pat. Nos. 4,588,394; 4,681,560; and 5,085, 644 the contents of which are included herein by reference and comprise devices whereby a pumping chamber is connected via a catheter directly into the body and derives its source of drug from a holding reservoir. The pumping chambers are of the form whereby they are biased to a maximum volume condition and on activation by the patient it is moved to a minimum volume position. In the case of U.S. Pat. No. 5,085,644 the entry of drug into the pumping chamber is controlled by means of a capillary such that the pump is only able to deliver a full volume after a predetermined period of time. The disadvantage with this form of delivery means however is that the drug levels within the body will vary periodically whereby on activation of the pump the drug level within the body initially is at a high level which is then allowed to decay over a period of time until the pump is reactivated.

In addition the prior art devices do not provide for a variety of dosage regimes. For instance in some circumstances it may be desirable to provide a substantially constant dosage rate over a period of time. In other circumstances it may be desirable to provide a dosage rate which decays over a period of time from a maximum level and where with repeated activation of the device the dosage rate can be maintained at a generally constant level for an extended period of time. In other instances it may be appropriate that at each dosage occasion the volume of drug which is to be delivered may need to be varied according to the circumstances of the patient.

According to one embodiment of the invention the drug delivery means is capable of a delivery of the drug at a generally constant flow rate between dosage occasions. This is achieved in one particular form of the embodiment by providing a delivery reservoir having a high volume relative to the flow rate of the flow restriction means. According to a preferred feature of the embodiment the pressure induced on the fluid within the delivery reservoir between the dosage occasions is generally constant.

According to another embodiment of the invention the drug delivery means is capable of a delivery of the drug at a decaying flow rate between dosage occasions. This is achieved in one particular form of the embodiment by providing a delivery reservoir having a low volume relative to the flow rate of the flow restriction means.

According to a preferred feature of the invention a bacterial filter is provided between the delivery reservoir and the flow restriction means. According to one particular embodiment the filter is adapted to enable gas to separate from the liquid passing to the filter and has a gas outlet for the gas which opens into the holding reservoir. It can be a further feature of the embodiment that the filter is accommodated within the holding chamber.

According to a further preferred feature the holding reservoir is associated with a filling port.

According to a further preferred feature of the invention the pump is accommodated on or within the holding reservoir.

In one form the control means comprises a first valve between the holding reservoir and the pump and a second valve between the pump and the delivery reservoir, said first and second valves permitting unidirectional flow to the pump and delivery reservoir respectively when the delivery reservoir is not filled to its maximum volume and the pressure within the delivery reservoir is less than the predetermined pressure, the second valve permitting fluid flow back to the holding reservoir when the pressure within the delivery reservoir is at least equal to the predetermined pressure.

According to an alternative form the control means comprises a unidirectional first valve between the holding reservoir and pump and a relief chamber between the pump and the first and second valve respectively, said relief chamber being resiliently expandable with the expandable portion of the wall of the relief chamber having a higher modulus of elasticity than the expandable portion of the delivery reservoir whereby the expandable portion of the relief chamber will expand on the pressure between the pump and the first and second valve respectively being at least equal to the predetermined pressure.

In another form the control means may comprise a relief valve communicating with the delivery reservoir which will permit the flow from the delivery reservoir to the holding reservoir where the fluid pressure in the delivery reservoir is at least equal to the predetermined pressure.

According to a preferred feature of each of the forms of the invention described above the valves are located within the holding reservoir.

According to a preferred feature of the invention the flow restriction means is formed with a plurality of flow pathways. In one form the flow restriction may comprise a plurality of capillary passageways or pores. This can be effected by utilisation of a porous element which can be formed of a glass, a ceramic or a like inert material.

According to an alternative preferred feature to that of the preceding paragraph invention the flow restriction means comprises a single flow path.

The invention will be more fully understood in the light of the following description of one specific embodiment. The description is made with reference to the accompanying drawings of which:

Figure 6:
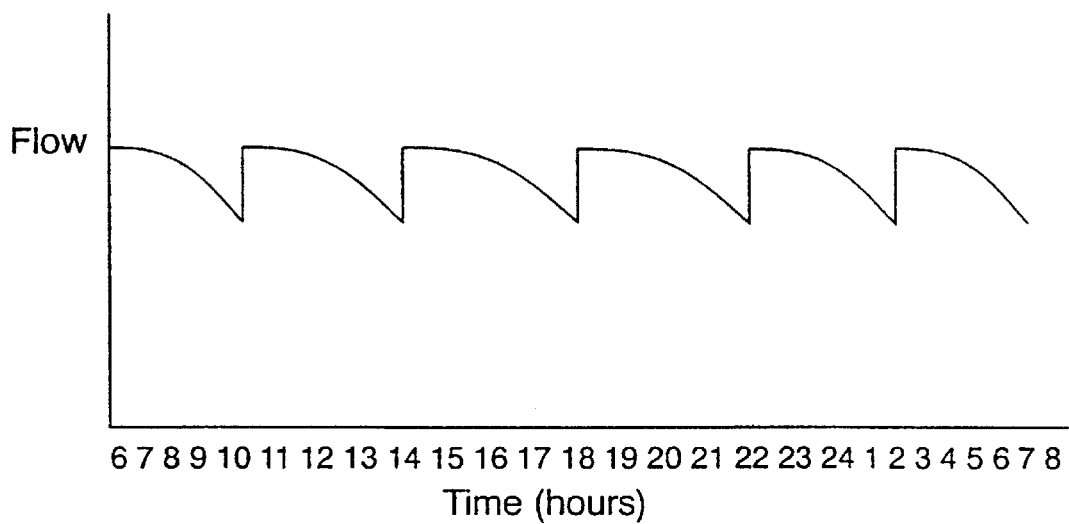

FIG. 6 is graphical illustration of the delivery capacity of the third embodiment as a result of a number of relatively closely spaced activations; and Each of the embodiment is directed to a drug delivery means which is a development beyond that which is disclosed in PCT/AU94/00469. It is a feature of each of the embodiments that the drug delivery means is of a unitary structure which simplifies packaging and utilisation.

Each of the embodiments may be mounted subcutaneously however it should be appreciated that the invention need not be so limited.

Figure 3:
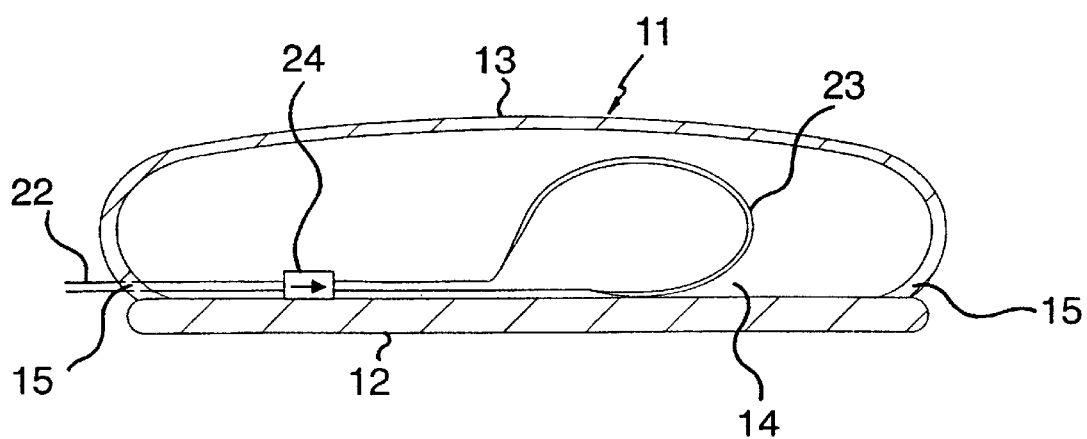
FIG. 3 is a sectional elevation of the holding reservoir according to either of the above embodiments.

The first embodiment comprises a holding reservoir 11 which is defined by a semi-rigid or substantially rigid planar circular base 12 (see FIG. 3) which has mounted thereto an expandable bladder element 13 formed of a flexible inert sheet material and which has a generally cylindrical configuration with one open face 14 where the edges 15 of the open face are bonded to the periphery of the base 12 at the edges thereof. The holding reservoir 11 is associated with a manually operable pump 16 which is external to the holding reservoir and is connected to the interior of the holding reservoir through a first fluid line 17. In addition the holding reservoir 11 is connected to an injection port 18 which corresponds generally to the form of injection port disclosed in U.S. Pat. No. 5,137,529 the contents of which are incorporated herein by reference. The injection port 18 is connected to the interior of the holding reservoir 11 through a second fluid line 19.

The pump comprises a chamber formed with a flexible wall which is biased to a maximum volume condition hereby on compression of the chamber its contents are forced from the chamber and on its expansion fluid is drawn into the chamber. The pump is intended to be located in the region of a bony prominence such as the sternum such that it is readily accessible to finger pressure from the patient.

The inner end of the first fluid line 17 from the pump 16 is bifurcated to provide two secondary lines 20 and 22, whereby the first secondary line 20 is in open communication with the interior of the holding reservoir 11 and is provided with a first control valve 21 while the second secondary line 22 is connected into the interior of a delivery reservoir 23 and is provided with a second control valve 24. The first and second control valves 21 and 24 are unidirectional and are such that on activation by the pump 16 fluid will flow from the interior of the holding reservoir through the first secondary line 20 and first control valve 21 into the second secondary line 22 and second control valve 24 to the delivery reservoir 23.

The delivery reservoir is formed to be resiliently expandable and is such that it can be expanded to a maximum volume whereby on it approaching its maximum volume the pressure which is applied to the liquid within the delivery chamber 23 is generally constant up to the maximum volume. The delivery chamber 23 is connected to an outlet 25 which may be connected to a catheter or a suitable infusion means.

The connection between the delivery reservoir 23 and the outlet 25 is effected through third fluid line 28 which includes a bacterial filter 26 and a flow restriction means 27. This serves to restrict the flow of liquid to the outlet 25 to a substantially constant low rate when subjected to the constant delivery pressure from the delivery reservoir 23. The flow restriction means may comprise a porous element formed of glass or a like ceramic material. An alternative form of flow restriction device can comprise a length of capillary tube.

The anti bacterial filter 26 comprises an antibacterial air venting filter and is provided with a first filter element which is able to filter from the liquid passing to the restriction device any particles and bacteria being carried by the medium. In addition the filter accommodates a gas filter 31 which enables the gas to permeate from the liquid. The gas filter is provided with an outlet 32 which opens into the holding reservoir 11.

In addition the third fluid line 28 which is provided between the delivery reservoir 23 and the filter 26 is provided with a relief line which opens into the interior of the holding reservoir 11 and is associated with a pressure relief valve 30. The pressure relief valve is such that it will open to permit fluid flow from the third fluid line 28 to the interior of the holding reservoir 11 to allow the flow of fluid from the third line to the holding reservoir when the pressure in the delivery reservoir exceeds a predetermined pressure whereby that predetermined pressure is only achieved on the delivery reservoir attaining its maximum volume.

The volume of the delivery reservoir is significantly greater than the flow rate of the flow restriction means 27 in order that the delivery reservoir is only partially emptied between each scheduled activation of the pump. For instance if the flow rate is set at 0.12 mls/hour and if the volume of the delivery reservoir is 15 ml and the scheduled activation of the pump is once per day then the delivery reservoir chamber is only partially emptied when it is refilled each day. As a result the pressure applied to the contents of the delivery reservoir between each scheduled activation is generally constant.

Figure 4:
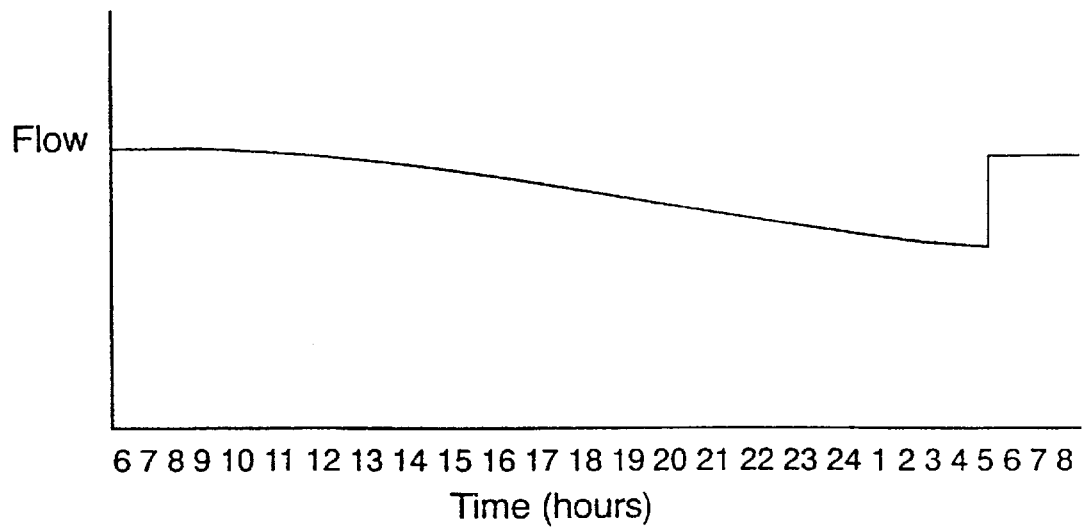
FIG. 4 is a graphical illustration of the delivery capacity of each of the embodiments.

The first embodiment provides a drug delivery means whereby delivery reservoir can be filled from the holding reservoir 11 through the pump 16 to a maximum volume but cannot be filled beyond that maximum volume due to the presence of the relief valve 30. In addition once the delivery reservoir has been filled with liquid to its maximum volume the fluid contained within the delivery reservoir 23 will be subjected to a generally constant pressure over a period of time which serves to force the liquid contained within the delivery reservoir to the outlet 25 at a generally constant flow rate over that period of time which flow rate is controlled by the flow restriction means 27. As a result the first embodiment is able to provide a generally constant flow of a desired drug to an infusion site over a period of time between scheduled activation as is graphically illustrated at FIG. 4. It is intended that in use, on each scheduled activation of the pump 16 the delivery reservoir is filled to its maximum volume.

It is a feature of the embodiment however that as the delivery reservoir 23 cannot be filled beyond its maximum volume irrespective of the degree of activation of the pump 16 the flow of the drug is substantially constant. Therefore repeated activation of the pump within the scheduled activation times will not result in an overdosing of the patient.

It is also a feature of the first embodiment that the pump has a unitary construction in that the delivery reservoir, control valves, filter and flow restriction means are all accommodated within the unitary construction of the holding reservoir. If the device is mounted subcutaneously it can be located in any suitable body cavity whilst the pump 16 can be located at a suitable location to facilitate its manipulation and the injection port 18 can be located at another suitable location to facilitate injection of the drug into the holding reservoir to refill the holding reservoir. It is also a feature of the embodiment that if the delivery reservoir should burst or leak its contents will pass into the holding reservoir.

Figure 1:
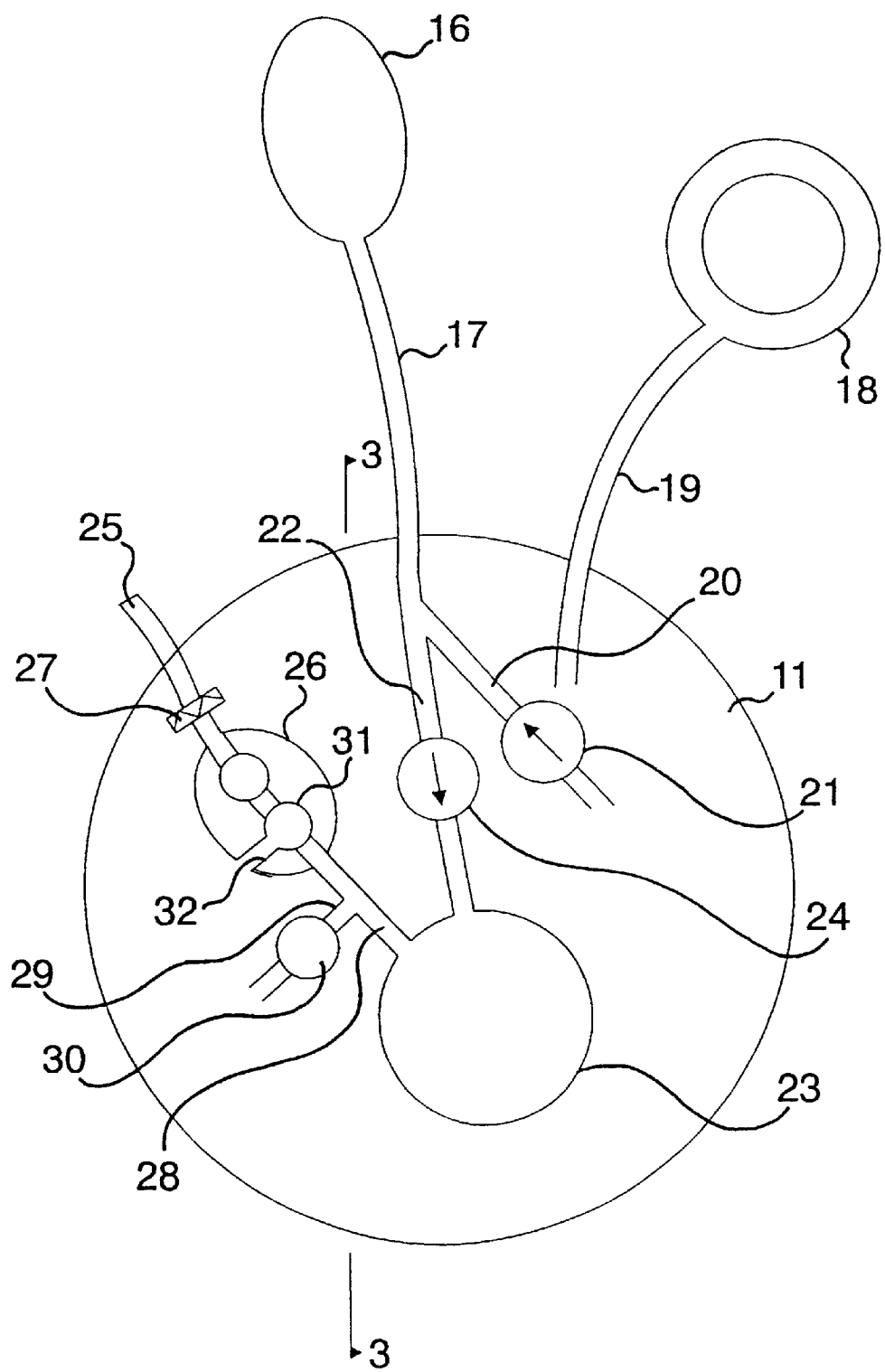
FIG. 1 is a schematic arrangement of the first embodiment.
Figure 2:
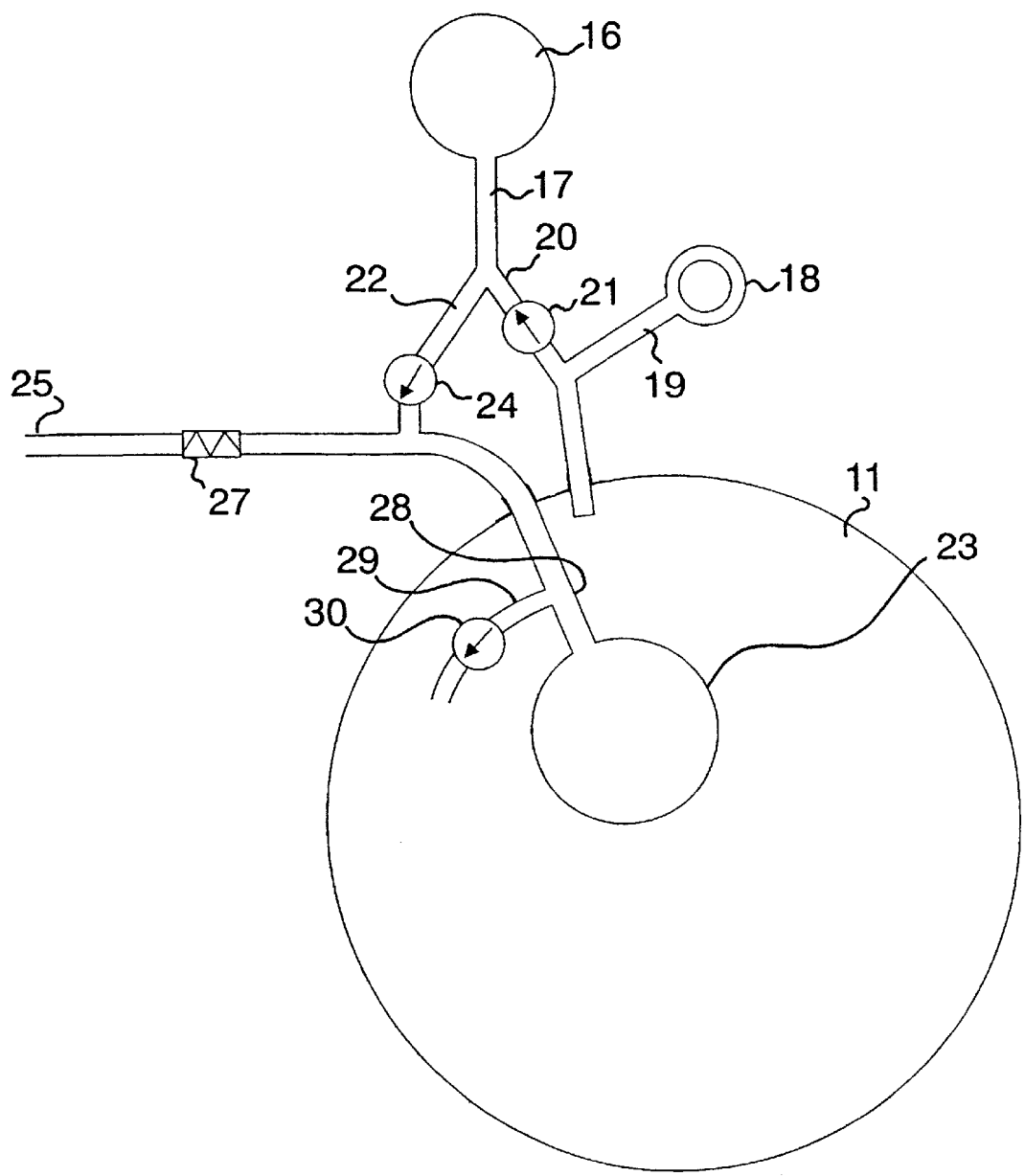
FIG. 2 is a schematic arrangement of the second embodiment.

The second embodiment shown at FIG. 2 is generally of a similar form to that of the first embodiment and as a result corresponding reference numerals have been used in respect of corresponding components. The essential difference between the second embodiment and first embodiment is that the third line 28 between the delivery reservoir 23 and the flow restrictor 27 does not incorporate an air venting filter as was the case in the first embodiment. In addition the first and second control valves and their associated connecting lines are located externally of the holding reservoir. In all other respects the second embodiment is of the same form as the first embodiment and operates in the same manner.

The advantage of the second embodiment as described above is that the flow restictor 27 is located externally of the main body 11. This allows the flow restictor 27 to be easily replaced or services at any desired point in time.

Figure 5:
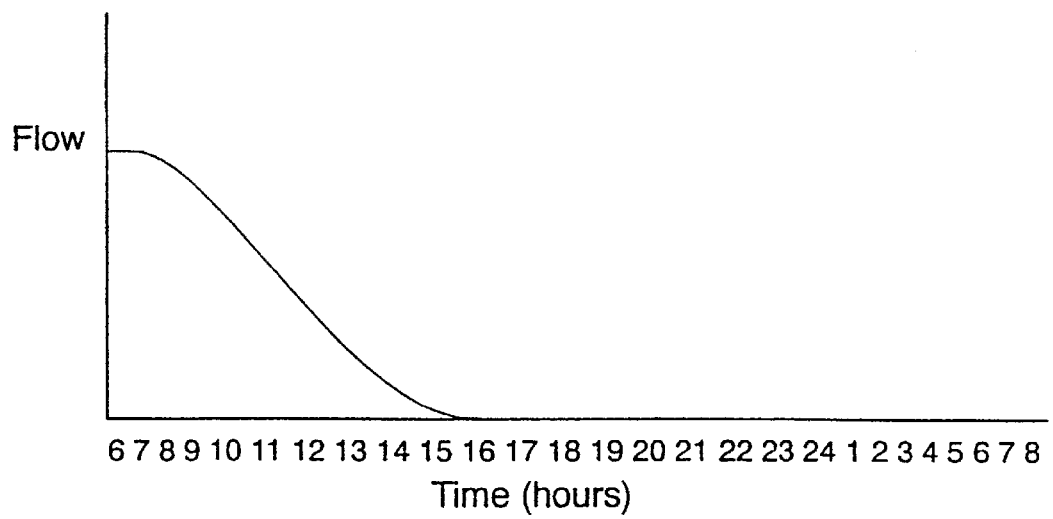
FIG. 5 is graphical illustration of the delivery capacity of the third embodiment as a result of a single activation.

A third embodiment of the invention is of corresponding form to the first embodiment and differs from the first embodiment in relation to the relative volume of the delivery reservoir. In the case of the third embodiment the volume of the delivery reservoir is small relative to the flow rate of the flow restriction means 27 in order that the delivery reservoir may be completely or significantly emptied between each scheduled activation of the pump. For instance if the maximum flow rate is set at 0.12 mls/hour and the maximum volume of the delivery reservoir is 3 ml with the scheduled activation of the pump once per day. As a result the delivery reservoir chamber is almost empty when it is refilled each day. As a result the pressure applied to the contents of the delivery reservoir between each scheduled activation will vary between scheduled activations. FIG. 5 is a graphical illustration of a dosage from the third embodiment over a period of time as a result of a single activation. FIG. 6 is a graphical illustration of the dosage from the third embodiment as a result of closely spaced repeated activations over a period of time whereby a generally constant delivery of drug is delivered during that period of time.

The third embodiment provides a means whereby the patient is able to control the delivery of drug according to the patient's requirements and the nature of the ailment being treated. As a result the embodiment is able to be used in the treatment of ailments such as diabetes where the need for insulin after a meal is fairly immediate and it is desired that the delivery of insulin is over a period of time at a decaying delivery rate.

The third embodiment provides a means whereby the dosage can be varied according to the needs of the patient. This is effected by calibrating the pump such that for each compression of the pump a known quantity of drug is delivered to the delivery reservoir. Therefore by activating the pump a requisite number of times at any one occasion the patient is able to establish a dosage on that occasion according to the needs of the occasion. In this instance it would be expected that the delivery reservoir will be at its minimum pressure before the pump is reactivated.

According to a further embodiment of the invention the injection port of each of the above embodiments is incorporated into the pump whereby fluid can be introduced into the holding reservoir through the delivery reservoir and against the forces required to inflate the delivery chamber. In addition such an arrangement enables fluid to be aspirated from the holding reservoir through the first secondary line and the first control valve.

According to a further embodiment of the invention the first and second control valves may comprise bidirectional valves where the valves will permit fluid flow in one direction while the upstream pressure is less than the predetermined pressure to effect the filling of the delivery reservoir to the maximum volume. However on the upstream pressure exceeding the predetermined pressure the valves will permit fluid flow in the opposite direction until the upstream pressure drops to the predetermined pressure or a second pressure below the predetermined pressure. In such a case the relief valve is no longer necessary.

It should be appreciated that the scope of the present invention need not be limited to the particular scope of the embodiment described above.

The claims defining the invention are as follows:

1. A drug delivery device comprising a holding reservoir, a pump, a delivery reservoir and an outlet, said holding reservoir being connected to said delivery reservoir through said pump by a connection, said pump being operable manually whereby fluid is transferred from the holding reservoir to the delivery reservoir, said delivery reservoir being connected to the outlet through a flow restriction which controls flow to the outlet, said delivery reservoir being resiliently expandable to a maximum volume wherein the connection between the holding reservoir and the delivery reservoir permits flow only from the holding reservoir to the delivery reservoir while the pressure within the delivery reservoir is less than a maximum pressure, said connection having a control device for redirecting flow to the holding reservoir upon the pressure within the delivery reservoir attaining said maximum pressure, said delivery reservoir being accommodated within the holding reservoir.

2. A drug delivery device as claimed at claim 1 which is capable of a delivery by a generally constant flow rate between dosage occasions.

3. A drug delivery device as claimed by claim 2 wherein the delivery reservoir has a high volume relative to the flow rate of the flow restriction means.

4. A drug delivery device as claimed by claim 2 wherein the pressure induced on the fluid within the delivery reservoir between intended dosage occasions is generally constant.

5. A drug delivery device as claimed at claim 1 which is capable of a delivery by a decaying flow rate between dosage occasions.

6. A drug delivery device as claimed by claim 5 wherein the delivery reservoir has a low volume relative to the flow rate of the flow restriction.

7. A drug delivery device as claimed by claim 1 wherein a bacterial filter is provided between the delivery reservoir and the flow restriction.

8. A drug delivery device as claimed by claim 7 wherein the filter is adapted to enable gas to separate from the liquid passing to the filter and has a gas outlet for the gas which opens into the holding reservoir.

9. A drug delivery device as claimed by claim 7 wherein the filter is accommodated within the holding reservoir.

10. A drug delivery device as claimed by claim 1 wherein the holding reservoir is associated with a filling port.

11. A drug delivery device as claimed by claim 1 wherein the pump is accommodated on or within the holding reservoir.

12. A drug delivery device as claimed by claim 1 wherein the control comprises a first valve between the holding reservoir and the pump and a second valve between the pump and the delivery reservoir, said first and second valves permitting unidirectional flow to the pump and the delivery reservoir respectively when the delivery reservoir is not filled to its maximum volume and the pressure within the delivery reservoir is less than the predetermined pressure, the second valve permitting fluid flow to the holding reservoir when the pressure within the delivery reservoir is at least equal to the predetermined pressure.

13. A drug delivery device as claimed by claim 1 wherein the control comprises a unidirectional first valve between the holding reservoir and pump and a relief chamber between the pump and the first or second valve respectively, said relief chamber being resiliently expandable with the expandable portion of the wall of the relief chamber having a higher modulus of elasticity than the expandable portion of the delivery reservoir whereby the expandable portion of the relief chamber will expand on the pressure between the pump and the delivery reservoir being at least equal to the predetermined pressure.

14. A drug delivery device as claimed by claim 1 wherein the control comprises a relief valve communicating with the delivery reservoir which will permit the flow from the delivery reservoir to the holding reservoir where the fluid pressure in the delivery reservoir is at least equal to the predetermined pressure.

15. A drug delivery device as claimed by claim 13 wherein the valves are located within the holding reservoir.

16. A drug delivery device as claimed by claim 1 wherein the flow restriction is formed with a plurality of flow pathways.

17. A drug delivery device as claimed by claim 16 wherein the flow restriction comprises a plurality of capillary passageways or pores.

18. A drug delivery device as claimed by claim 16 wherein the flow restriction comprises a porous element which is formed of a glass, a ceramic or other material.

19. A drug delivery device as claimed by claim 16 wherein the flow restriction comprises a single flow path.

* * * * *